US009149555B2

(12) United States Patent
Smith

(10) Patent No.: US 9,149,555 B2
(45) Date of Patent: *Oct. 6, 2015

(54) OPHTHALMIC AND CONTACT LENS SOLUTIONS USING CARNITINE

(71) Applicant: FXS Ventures, LLC, Salem, NH (US)

(72) Inventor: Francis X. Smith, Salem, NH (US)

(73) Assignee: FXS Ventures, LLC, Salem, NH (US)

( * ) Notice: Subject to any disclaimer, the term of this patent is extended or adjusted under 35 U.S.C. 154(b) by 48 days.

This patent is subject to a terminal disclaimer.

(21) Appl. No.: 13/870,094

(22) Filed: Apr. 25, 2013

(65) Prior Publication Data

US 2013/0233734 A1 Sep. 12, 2013

Related U.S. Application Data

(60) Division of application No. 13/195,389, filed on Aug. 1, 2011, now abandoned, which is a continuation of application No. 10/294,509, filed on Nov. 14, 2002, which is a continuation of application No. 09/706,317, filed on Nov. 4, 2000, now abandoned.

(51) Int. Cl.
| | |
|---|---|
| *A61K 31/74* | (2006.01) |
| *A61L 12/12* | (2006.01) |
| *A01N 33/12* | (2006.01) |
| *A01N 37/44* | (2006.01) |
| *A01N 43/38* | (2006.01) |
| *A01N 43/50* | (2006.01) |
| *A01N 47/44* | (2006.01) |
| *A61L 12/08* | (2006.01) |
| *A61L 12/14* | (2006.01) |
| *A45C 11/00* | (2006.01) |
| *C09D 5/00* | (2006.01) |
| *A61L 2/18* | (2006.01) |

(52) U.S. Cl.
CPC ............... *A61L 12/12* (2013.01); *A01N 33/12* (2013.01); *A01N 37/44* (2013.01); *A01N 43/38* (2013.01); *A01N 43/50* (2013.01); *A01N 47/44* (2013.01); *A45C 11/005* (2013.01); *A61L 2/18* (2013.01); *A61L 12/086* (2013.01); *A61L 12/143* (2013.01); *C09D 5/00* (2013.01)

(58) Field of Classification Search
USPC ........................................ 424/78.04; 514/786
See application file for complete search history.

(56) References Cited

U.S. PATENT DOCUMENTS

| | | |
|---|---|---|
| 3,428,576 A | 2/1969 | Dickinson |
| 4,022,834 A | 5/1977 | Gundersen |
| 4,029,817 A | 6/1977 | Blanco |
| 4,046,706 A | 9/1977 | Krezanoski |
| 4,599,360 A | 7/1986 | Fukami |
| 4,783,488 A | 11/1988 | Ogunbiyi |
| 4,836,986 A | 6/1989 | Ogunbiyi |
| 4,863,900 A | 9/1989 | Pollock |
| 4,891,423 A | 1/1990 | Stockel |
| 4,997,626 A | 3/1991 | Dziabo |
| 5,030,721 A | 7/1991 | Kasai |
| 5,439,572 A | 8/1995 | Pankow |
| 5,547,990 A | 8/1996 | Hall |
| 5,607,681 A | 3/1997 | Galley |
| 5,612,375 A | 3/1997 | Sueoka |
| 5,660,862 A | 8/1997 | Park |
| 5,674,450 A | 10/1997 | Lin |
| 5,691,379 A | 11/1997 | Ulrich |
| 5,719,110 A | 2/1998 | Cook |
| 5,770,582 A | 6/1998 | von Borstel |
| 5,807,585 A | 9/1998 | Martin |
| 5,811,446 A | 9/1998 | Thomas |
| 5,840,671 A | 11/1998 | Fujimura |
| 5,869,468 A | 2/1999 | Freeman |
| 5,968,904 A | 10/1999 | Julian |
| 6,001,805 A | 12/1999 | Jaynes |
| 6,117,869 A | 9/2000 | Picard |
| 6,121,327 A | 9/2000 | Tsuzuki |
| 6,139,646 A | 10/2000 | Asgharian |
| 6,153,568 A | 11/2000 | McCanna |
| 6,191,110 B1 | 2/2001 | Jaynes |
| 6,242,491 B1 | 6/2001 | Kaddurah-Daouk |
| 6,482,799 B1 | 11/2002 | Tusé |
| 6,617,291 B1 | 9/2003 | Smith |
| 7,939,501 B2 | 5/2011 | Smith |
| 8,093,352 B2 | 1/2012 | DeSousa |
| 8,247,461 B2 | 8/2012 | Smith |
| 2003/0190258 A1 | 10/2003 | Smith |
| 2007/0098818 A1 | 5/2007 | Smith |
| 2007/0110782 A1 | 5/2007 | Smith |
| 2007/0149428 A1 | 6/2007 | Ammon |
| 2007/0196329 A1 | 8/2007 | Xia |
| 2008/0110770 A1 | 5/2008 | Burke |
| 2012/0017806 A1 | 1/2012 | Smith |

FOREIGN PATENT DOCUMENTS

| | | |
|---|---|---|
| JP | 2006198001 | 8/2006 |
| WO | WO2012172274 | 12/2012 |

OTHER PUBLICATIONS

Derwent Abstract 2001053625; "Solutions for Preventing drying of contact lens" (2 pages).
Sharma; Biomater Artif Cells Immobilization Biotechnol 1992; 19(3):599-612; "Surface modification of Corneal Contact Lens with phosphoryl choline by glow discharge".

*Primary Examiner* — Zohreh Fay
(74) *Attorney, Agent, or Firm* — Christopher E. Blank, Esq.; Peter J. Mikesell; Schmeiser, Olsen & Watts, LLP

(57) ABSTRACT

The present invention relates to a lens care solution having 0.001 to about 5 weight percent of a low molecular weight amine of the general formula:

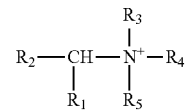

where $R_1$, $R_2$, $R_3$ and $R_4$ are —H or low molecular weight radicals, and $R_5$ is a low molecular weight radical, or salt thereof; an effective amount of a tonicity agent; and the balance water.

4 Claims, No Drawings

OPHTHALMIC AND CONTACT LENS SOLUTIONS USING CARNITINE

CROSS-REFERENCE TO RELATED APPLICATIONS

This application is a divisional of Ser. No. 13/195,389 (filed Aug. 1, 2011) which is a continuation of U.S. Ser. No. 10/294,509 (filed Nov. 14, 2002) which is a continuation application of U.S. Ser. No. 09/706,317 (filed Nov. 4, 2000), now abandoned. The content of each of the aforementioned patent applications is hereby incorporated by reference.

STATEMENT REGARDING FEDERALLY FUNDED RESEARCH OR DEVELOPMENT

This invention was made with support from a government grant under grant number EY11572 from the National Institute of Health. The government has retained certain rights in this invention.

SUMMARY OF THE INVENTION

The present invention relates to contact lens care solutions that have improved ability to resist protein deposition and to provide lenses treated with such solutions to stabilize proteins more effectively, and to decrease the degree of other cationic depositions on said lenses, such as cationic preservative deposition of the lenses. The solutions of the present invention employ short chain quaternary amines as an additive to state of the solutions in order to decrease the denaturation of proteins during cleaning cycles and to coat treated lenses to decrease the number of active binding sites on the lenses. The sort chain quaternary amines are of the general chemical formula:

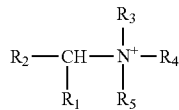

where $R_{1-5}$ generally is a short chain of 1 to 4 carbon atoms with hydroxyl or carboxylic acid functionality or a salt thereof. In particular $R_{1-5}$ may be chosen to be carnitine, betaine, or choline or salts thereof. These cationic amines also provide increased preservative efficacy, reduce the potential for irritation by decreasing the possibility of cationic preservative binding on lenses, and furthermore act as buffering agents to provide increased pH stability for prepared solutions. Specifically $R_1$, $R_2$, $R_3$ and $R_4$ are —H or from the group of radicals below, or salts thereof, and $R_5$ is chosen from the group of radicals below, or salts thereof:

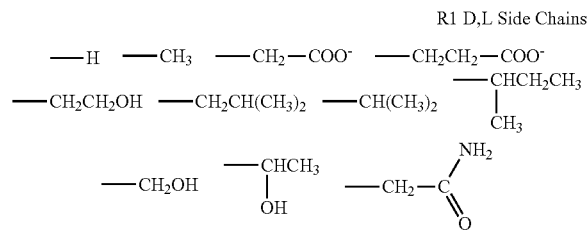

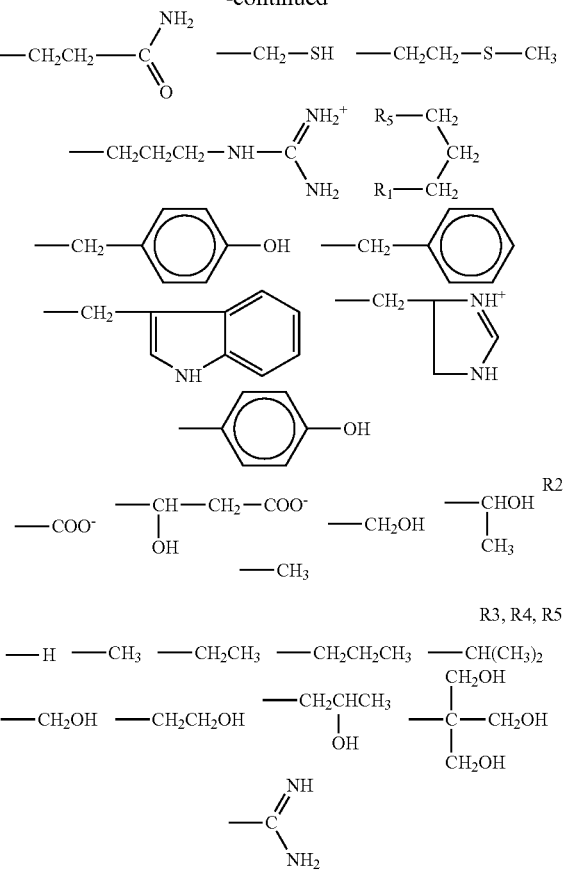

Specifically compounds that meet the requirements of the present invention as an amine include, but are not limited to Betaine; Bicine (N,N-Bis(2-hydroxyethyl)-glycline); Bis-Tris (Bis-(2-hydroxyethyl)imino-tns (hydroxymethyl) methane; Choline; Carnitine; Creatine; Creatinine; Diisopropylamine; Diethanolamine; dimethyl Aspartic Acid; Dimethyl glutamate; Methyl Aspartate; Methylethanolamine; Hydroxymethyl Glycinate; Triethylamine; Triethanolamine; Tricine(N-tris(hydroxymethyl)methyl glycine); and Triisopropanolamine, and the like.

Protein binds to contact lens and form tenacious deposits that must be removed by mechanical rubbing or enzymatic hydrolysis. Physiologic problems associated with antigenic response to the denatured protein. Adversely affects optical clarity. Since denatured proteins are hydrophobic, heavily deposited lenses will feel dry and uncomfortable. Therefore, systems that are able to reduce protein adsorption will result in improved quality of wear for the individual.

It is thought that contact lens have a net negative charge. Cationic protein will preferentially bind to these lenses. The low molecular weight amines will compete for the bind sites and reduce the amount of protein that is deposited. The strength of competition is based on the binding strength of the competing amine. Quaternary amines are recognized as strong binding groups whose charge is independent of pH. Progressive substitution of the quaternary group is acceptable providing the pH is controlled to ensure an cationic charge. Removing more than three of the substituents will result in a primary amine which has the potential for binding to reducing sugars such as glucose and form a colored Schiff Base reaction product. Therefore, the preferred compounds are secondary, tertiary, and quaternary low molecular weight amines with at least one hydrophilic substituent.

Methods of Use

The solution of the present invention are may be used in several modes: preferably, the solutions are used to pre-treat the lens with the low molecular weight (LMW) amines prior to insertion. These LMW amines are added to the isotonic aqueous lens vial solution. The solution may be buffered or the amines may act as their own buffer to control the pH. The solution should be isotonic (150-450 mOsm) in order to ensure the full lens matrix is properly hydrated and the sites are available for binding. The pH should be approximately neutral (4.5 to 8.5). This will ensure the lenses that rely on carboxylic acids for lens hydration are fully ionized at a pH above 4.5. The amines are cationic at a pH below 8.5 and therefore function well to prevent protein deposition at physiological pH ranges.

The solutions may also be used to repetitively treat contact lenses with the LMW amines to replenish any material that may have dissociated from the lens during wear. In this case, since the solution is generally preserved with a cationic preservative, these amines will compete with the cationic preservative for binding to the lens, and provide further advantages in reducing contact lens discomfort.

Lastly the solutions may be applied directly to lenses while on the eye to replenish any material that has dissociated from the lens during wear.

Formulations

The present invention comprises 0.0001 to 5 weight percent of short chain quaternary amines (the LMW amines described above) and a second contact lens solution agent. These agents may include but are not limited to an effective amount of a preservative component, for example, an effective preserving amount of a non-oxidative antimicrobial component. Any suitable preservative component may be employed provided that it functions as a preservative and has no significant detrimental effect on the contact lens being treated or the wearer of the treated contact lens. Examples of useful preservative components include, but are not limited to, poly[dimethylimino-2-butene-1,4-diyl]chloride, alpha [4-tris (2-hydroethyl) ammonium-dichloride (available from Onyx Corporation under the trademark Polyquarternium I Registered™), benzalkonium halides such as benzalkonium chloride, alexidine salts, chlorhexidine salts, hexamethylene biguanides and their polymers, and the like and mixtures thereof.

The amount of preservative component included varies over a relatively wide range depending, for example, on the specific preservative component being employed. Preferably, the amount of preservative component is in the range of about 0.000001% to about 0.001% or more.

The liquid media, e.g., aqueous liquid media, employed preferably include a buffer component which is present in an amount effective to maintain the pH of the liquid medium in the desired range. This buffer component may be present in the liquid medium, e.g., either separately or in combination with one or more of the other presently useful components, e.g., with the hydrogen peroxide. Among the suitable buffer components or buffering agents which may be employed are those which are conventionally used in contact lens care products. Examples of useful buffer components include those with carbonate functionalities, bicarbonate functionalities, phosphate functionalities, borate functionalities, and amine functionalities the like and mixtures thereof. The buffers may be alkali metal and alkaline earth metal salts, in particular sodium and potassium.

Further, in order to avoid possible eye irritation, it is preferred that the presently useful combined liquid medium has an osmolality (a measure of tonicity) of at least about 200 mOsmollkg, preferably in the range of about 200 to about 350 or abou 400 mOsmollkg. In an especially useful embodiment, the osmolality or tonicity o the combined liquid medium substantially corresponds to the tonicity of the fluids of the eye, in particularly the human eye.

Any suitable ophthalmically acceptable tonicity component or components may be employed, provided that such component or components are compatible with the other ingredients of the combined liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof The amount of ophthalmically acceptable tonicity component utilized can vary widely. In one embodiment, the tonicity component is preferably present in the combined liquid medium in an amount in the range of about 0.5 to about 0.9% of the combined liquid medium.

One or more additional components can be included in one or more of the present useful liquid media. Such additional component or components are chosen to impart or provide at least one beneficial or desired property to the liquid media. Such additional components may be selected from components which are conventionally used in one or more contact lens care compositions and which do not detrimentally interact with the other components present. Examples of such additional components include cleaning agents, wetting agents, nutrient agents, sequestering agents, viscosity builders, contact lens conditioning agents, colorants, and the like. These additional components may each be included in the combined liquid medium in an amount effective to impart or provide the beneficial or desired property to the combined liquid medium. Such additional components may be included in the presently useful liquid media in amounts similar to the amounts of such components used in other, e.g., conventional, contact lens care products.

Examples of useful sequestering agents include disodium ethylenediamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

In a particularly useful embodiment further includes at least one enzyme effective to remove debris or deposit material from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Reissue Pat. No. 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof. Preferred proteolytic enzymes are those which are substantially free of sulfhydryl groups or disulfide bonds, whose presence may react with the active oxygen in the HPLM to the detriment of the activity of the enzyme.

Metallo-proteases, those enzymes which contain a divalent metal ion such as calcium, magnesium or zinc bound to the protein, may also be used.

A more preferred group of proteolytic enzymes are the serine proteases, particularly those derived from *Bacillus* and *Streptomyces* bacteria and *Aspergillus* molds. Within this grouping, the still more preferred enzymes are the derived alkaline proteases generically called subtilisin enzymes. Reference is made to Keay, L., Moser, P. W. and Wildi, B. S., "Proteases of the Genus *Bacillus*". II. Alkaline Proteases, "Biotechnology & Bioengineering", Vol. XII, pp. 2 13-249 (1970, March) and Keay, L. and Moser, P. W., "Differentiation of Alkaline Proteases form *Bacillus* Species" Biochemical and Biophysical Research Comm., Vol. 34, No. 5, pp. 600-604, (1969).

The subtilisin enzymes are broken down into two sub-classes, subtilisin A and subtilisin B. In the subtilisin A grouping are enzymes derived from such species are *B. subtilis, B. licenifomiis* and *B. pumilis*. Organisms in this sub-class produce little or not neutral protease or amylase. The subtilisin B. sub-class is made up of enzymes from such organisms a *B. subtilis, B. subtilis* var. *amylosachariticus, B. aniyloliquefaciens* and *B. subtilis* NRRL B341 1. These organisms product neutral proteases and amylases on a level about comparable to their alkaline protease production. One or more enzymes from the subtilisin A sub-class are particularly useful.

In addition other preferred enzymes are, for example, pancreatin, trypsin, collagenase, keratinase, carboxylase, aminopeptidase, elastase, and aspergillopeptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.00 1 to about 3 Anson units of activity, preferably about 0.01 to about 1 Anson units, per single lens treatment. Higher or lower amounts may be used. Enzyme activity is pH dependent so for any given enzyme, there is a particular pH range that is most effective and the solution may be formulated to adjust the pH for optimal enzyme activity.

EXAMPLE I

Reduced Protein Deposition

Contact lenses were soaked and heated in test solutions to which a radio-labeled lysozyme was present in a known amount for a period of 12 hours at 37 degrees Celsius. The lenses were rinsed with distilled water in order to remove residual solution. The lenses were then assayed for protein deposition using a Beckman BioGamma I counter. Results were reported in ug/lens.

|  | Lens A ug/lens | Lens B ug/lens | Average ug/lens |
|---|---|---|---|
| Phosphate buffer control | 1,043 | 865 | 954 |
| Choline Chloride (1%) in phosphate buffer | 14 | 9 | 12 |

Choline chloride was a 1 percent w/v solution. The matrix control was phosphate buffer and sodium chloride. The low molecular weight amine solution had lower protein binding than the control.

EXAMPLE 2

Reduced Preservative Binding

Contact lenses were soaked and heated in test solutions to which a radio-labeled $C^{14}$-PHMB solution in a known concentration for a period of 12 hours at 37 degrees Celsius. The lenses were rinsed with distilled water in order to remove residual solution. The lenses were then assayed for the radio-labeled protein deposition using a Beckman BioGamma 1 counter. Results were reported in ug/lens.

| Solution | Lens A ug/lens | Lens B ug/lens | Average ug/lens |
|---|---|---|---|
| 1% choline chloride in phosphate buffer | 18 | 11 | 14.5 |
| 1% carnitine in phosphate buffer | 9 | 13 | 11 |
| 1% betaine HCl in phosphate buffer | 6 | 8 | 7 |
| Phosphate buffer control | 73 | 64 | 68.5 |

Each of the additives were at a 1 percent w/v solution in the phosphate buffer. The control was phosphate buffer and sodium chloride. The low molecular weight amines solution had a lower cationic preservative adsorption the control.

EXAMPLE 3

Example of Protein Deposition Inhibition

Contact lenses were soaked test solutions overnight. Afterwards, lysozyme was added to the tubes and warmed to 37 degrees Celsius for 12 hours. The lenses were rinsed with distilled water in order to remove residual solution. The lenses were assayed for protein deposition by the BCA method and detected on an HP PDA Spectrophotometer. Results were reported in ug/lens.

| Solution | ug lysozyme per lens |
|---|---|
| Marketed Product Control (phosphate buffer, Poloxamer) | >18.3 |
| Phosphate buffer control | >26.16 |
| Choline chloride (1%) | 4.1 |
| Betaine HCl (1%) | 2.44 |

Choline chloride and Betaine HCl were a 1 percent w/v solution in the phosphate buffer. The control was phosphate buffer and sodium chloride. The low molecular weight amine solution had lower protein binding than the control.

EXAMPLE 3A

Improved Antimicrobical Activity

Formulations containing low molecular weight amines were prepared in a 0.1% phosphate buffer. The solutions were made isotonic with sodium chloride and preserved with polyhexamethylene biquanide at 0.0001% and hydrogen peroxide at 0.0060%. Dequest 2060S was added as a stabilizer. The pH was adjusted to 7.0 with either 1 N sodium hydroxide. The in vitro microbicidal activity of the solutions was determined by exposing $C.\ albicans$ to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

|  | $C\ albicans$ log reduction | Improvement |
|---|---|---|
| bicine (1%) | 0.75 | 0.34 |
| creatinine (1%) | 1.42 | 1.01 |
| buffer control | 0.41 |  |

Each of the low molecular weight amines showed an improvement in the activity against $C.\ albicans$ as compared to the buffer control.

EXAMPLE 4

Improved Antimicrobical Activity

Formulations containing exemplary low molecular weight amines were prepared in a 0.2% phosphate buffer. The solutions were made isotonic with sodium chloride and preserved with polyhexamethylene biquanide at 0.0001%. The pH was adjusted to 7.2 with either 1N sodium hydroxide or 1 N hydrochloric acid. The in vitro microbicidal activity of the solutions was determined by exposing $C.\ albicans$ to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

|  | $C\ albicans$ log reduction | Improvement |
|---|---|---|
| betaine HCl (0.5%) | 1.37 | 0.38 |
| bis-tris (0.5%) | 1.21 | 0.22 |
| carnitine (0.5%) | 1.28 | 0.29 |
| choline (0.5%) | 2.24 | 1.25 |
| creatine (0.5%) | 1.72 | 0.73 |
| tricine (0.5%) | 1.33 | 0.34 |
| triethylamine (0.5%) | 1.64 | 0.65 |
| triethanolamine (0.5%) | 1.82 | 0.83 |
| buffer control | 0.99 |  |

Each of the low molecular weight amines showed an improvement in the activity against $C.\ albicans$ as compared to the buffer control.

EXAMPLE 5

An example of a preferred disinfecting formulation of the subject invention is provided below in Table I. This solution is prepared by weighing out the necessary amount of the tricine, creatine, choline chloride, sodium chloride and edetate disodium into a vessel containing approximately 90% of the water volume. After each of the ingredients has dissolved, the pH is adjusted to 7.3 with either 1 N sodium hydroxide or 1 N hydrochloric acid. Following this, the polyhexamethylene biguanide is added and the solution is brought to final volume with purified water. The final product has the composition shown in the Table below.

TABLE 4

| Constituent |  | Weight/Volume |
|---|---|---|
| Polyhexamethylenebiguanide HCI | 20% w/w solution available under the mark Cosmocil CQ from Avecia | 0.0001% |
| Tricine |  | 1.0% |
| Creatine |  | 0.25% |
| Choline Chloride |  | 0.5% |
| Edetate Disodium |  | 0.055% |
| Polyoxyl 40 Hydrogenated Castor Oil | Cremophor RH 40 from BASF Co. | 0.1% |
| Sodium Chloride |  | As required for tonicity adjustment 300 mOsm |
| Hydrochloride Acid, 1N |  | as required for pH adjustment to 7.3 |
| Sodium Hydroxide, 1N |  | as required for pH adjustment to 7.3 |
| Purified Water |  | Balance to 100% |

This solution may be used to rinse, clean, and store contact lenses on a daily basis.

EXAMPLE 6

An example of a preferred formulation for a contact lens vial storage of the subject invention is provided below in Table I. This solution is prepared by weighing out the necessary amount of the tricine, creatine, choline chloride, and sodium chloride into a vessel containing approximately 90% of the water volume. After each of the ingredients has dissolved, the pH is adjusted to 7.3 with either 1 N sodium hydroxide or 1 N hydrochloric acid. Following this, the polyhexamethylene biguanide is added and the solution is brought to final volume with purified water. The final product had the composition shown in Table I below.

TABLE 4

| Constituent |  | Weight / Volume |
|---|---|---|
| Tricine |  | 1.0% |
| Creatine |  | 0.25% |
| Choline Chloride |  | 0.5% |
| Polyoxyl 40 Hydrogenated Castor Oil | Cremophor RH 40 from BASF Co. | 0.1% |
| Sodium Chloride |  | As required for tonicity adjustment 300 mOsm |
| Hydrochloride Acid, 1N |  | as required for pH adjustment to 7.3 |
| Sodium Hydroxide, 1N |  | as required for pH adjustment to 7.3 |
| Purified Water |  | Balance to 100% |

An example from another patent: specific representative embodiments of biguanides for use in the contact lens disinfectant methods include free bases and water soluble salts wherein:

EXAMPLE 8

Cleaning and Disinfecting Formulation

An example of a preferred cleaning and disinfecting formulation of the subject invention is provided. This solution is prepared by weighing out the necessary amount of the tricine, creatine, choline chloride, sodium chloride and edetate disodium into a vessel containing approximately 90% of the water volume. After each of the ingredients has dissolved, the pH is adjusted to 7.3 with either 1 N sodium hydroxide or 1 N hydrochloric acid. Following this, the polyhexamethylene biguanide is added and the solution is brought to final volume with purified water. The final product has the composition shown in the following table.

| Constituent | % Weight/Volume | Amount |
|---|---|---|
| Purified water | | 40 mL |
| Tricine | 1.0% | 0.500 g |
| Creatine | 0.25% | 0.125 g |
| Choline Chloride | 0.5% | 0.250 g |
| Edetate Disodium | 0.055% | 0.0275 g |
| Polyoxyl 40 Hydrogenated Castor Oil (Cremophor RH 40 from BASF Co.) | 0.1% | 0.5 mL of 10% |
| Polyhexamethylenebiguanide HCl (20% w/w solution available under the mark Cosmocil CQ from Avecia) | 0.0001% | 50 uL of 0.1% |
| Sodium Chloride | As required for tonicity adjustment 300 mOsm | As required for tonicity adjustment 300 mOsm |
| Hydrochloride Acid, 1N | as required for pH adjustment to 7.3 | as required for pH adjustment to 7.3 |
| Sodium Hydroxide, 1N | as required for pH adjustment to 7.3 | as required for pH adjustment to 7.3 |
| Purified Water | Balance to 100% | Dilute to 50 mL |

This solution may be used to rinse, clean, and store contact lenses on a daily basis.

EXAMPLE 8

Lens Vial Storage

An example of a preferred formulation for a contact lens vial storage of the subject invention is provided. This solution is prepared by weighing out the necessary amount of the tricine, creatine, choline chloride, and sodium chloride into a vessel containing approximately 90% of the water volume. After each of the ingredients has dissolved, the pH is adjusted to 7.3 with either 1 N sodium hydroxide or 1 N hydrochloric acid. Following this, the polyhexamethylene biguanide is added and the solution is brought to final volume with purified water. The final product had the composition shown in Table I below.

| Constituent | % Weight/Volume | Amount |
|---|---|---|
| Purified water | | 40 mL |
| Tricine | 1.0% | 0.500 g |
| Bis-Tris | 0.25% | 0.125 g |
| Polyoxyl 40 Hydrogenated Castor Oil (Cremophor RH 40 from BASF Co.) | 0.1% | 0.5 mL of 10% |
| Sodium Chloride | As required for tonicity adjustment 300 mOsm | As required for tonicity adjustment 300 mOsm |
| Hydrochloride Acid, 1N | as required for pH adjustment to 7.3 | as required for pH adjustment to 7.3 |
| Sodium Hydroxide, 1N | as required for pH adjustment to 7.3 | as required for pH adjustment to 7.3 |
| Purified Water | Balance to 100% | Dilute to 50 mL |

EXAMPLE 9

Disinfecting Solution

Formulation was prepared by dissolving Tricine, Carnitine, Betaine HCl, Choline Chloride, Inositol, Disodium edetate, and Cremophor RH40 in 80% of the water volume. The pH of the solution was adjust to 7.3 with 1 N sodium hydroxide. The tonicity of the solution was adjusted with sodium chloride and polyhexamethylene biguanide. The solution was diluted to volume with water.

| Constituent | Supplier | % Weight/Volume | Amount |
|---|---|---|---|
| Purified water | | to 80% | 40 mL |
| Tricine | Spectrum | 1.0% | 0.500 g |
| Carnitine | Spectrum | 0.25% | 0.125 g |
| Betaine HCl | Spectrum | 0.1% | 0.050 g |
| Choline Chloride | Amresco | 0.5% | 0.250 g |
| Inosito | Spectrum | 0.1% | 0.050 g |
| Edetate Disodium | Spectrum | 0.055% | 0.0275 g |
| Polyoxyl 40 Hydrogenated Castor Oil | Cremophor RH 40 from BASF Co. | 0.1% | 0.5 mL of 10% |
| Sodium Hydroxide, 1N | | as required for pH adjustment to 7.3 | as required for pH adjustment to 7.3 |
| Purified Water | | to 98% | Dilute to 49 mL |
| Sodium Chloride | Fisher | As required for tonicity adjustment 300 mOsm | As required for tonicity adjustment 300 mOsm |
| Polyhexamethylenebiguanide HCl | 20% w/w solution available under the mark Cosmocil CQ from Avecia | 0.0001% | 50 uL of 0.1% |
| Purified Water | | Balance to 100% | Dilute to 50 mL |

EXAMPLE 10

Lens Storage Solution (BCL1O6-037-3)

Formulation was prepared by dissolving Tricine, Carnitine, and Inositol in 80% of the water volume. The pH of the solution was adjust to 7.3 with 1 N sodium hydroxide and Cremophor RH40 was added. The tonicity of the solution was adjusted with sodium chloride. The solution was diluted to volume with water.

| Constituent | Supplier | % Weight/Volume | Amount |
|---|---|---|---|
| Purified water | | to 80% | 40 mL |
| Tricine | Spectrum | 1.0% | 0.500 g |
| Carnitine | Spectrum | 0.25% | 0.125 g |
| Inositol | Spectrum | 0.1% | 0.050 g |
| Hydrochloride Acid, 1N | | as required for pH adjustment to 7.3 | as required for pH adjustment to 7.3 |

-continued

| Constituent | Supplier | % Weight/Volume | Amount |
|---|---|---|---|
| Sodium Hydroxide, 1N | | as required for pH adjustment to 7.3 | as required for pH adjustment to 7.3 |
| Polyoxyl 40 Hydrogenated Castor Oil | Cremophor RH 40 from. BASF Co | 0.1% | 0.5 mL of 10% |
| Purified Water | | to 98% | Dilute to 49 mL |
| Sodium Chloride | Fisher | As required for tonicity adjustment 300 mOsm | As required for tonicity adjustment 300 mOsm |
| Purified Water | | to 100% | Dilute to 50 mL |

What is claimed is:

1. An ophthalmic product comprising:
at least one contact lens;
a contact lens container; and
a sufficient volume of a contact lens solution to wet the contact lens where the contact lens solution comprises 0.001 to about 5 weight percent of carnitine; an effective amount of biologically compatible buffer to maintain the pH of the solution between 5.5 and 8.5 pH; and the balance water.

2. The ophthalmic product of claim 1, wherein the contact lens solution consists essentially of the carnitine, the biologically compatible buffer, an effective amount of a tonicity agent, and the balance water.

3. The ophthalmic product of claim 1, wherein the contact lens solution consists essentially of the carnitine, the biologically compatible buffer, an effective amount of a tonicity agent, and a preservative and the balance water.

4. The ophthalmic product of claim 3, wherein the preservative is poly[dimethylimino-2-butene-1,4-diyl]chloride, alpha[4-tris(2-hydroethyl)ammonium-dichloride.

* * * * *